US00PP24632P2

(12) United States Plant Patent
Hansen

(10) Patent No.: US PP24,632 P2
(45) Date of Patent: Jul. 8, 2014

(54) ***SEDUM* PLANT NAMED 'LIME ZINGER'**

(50) Latin Name: ***Sedum* hybrid**
Varietal Denomination: Lime Zinger

(71) Applicant: Christopher M. Hansen, Holland, MI (US)

(72) Inventor: Christopher M. Hansen, Holland, MI (US)

( * ) Notice: Subject to any disclaimer, the term of this patent is extended or adjusted under 35 U.S.C. 154(b) by 124 days.

(21) Appl. No.: 13/573,635

(22) Filed: Sep. 27, 2012

(51) Int. Cl.
*A01H 5/00* (2006.01)

(52) U.S. Cl.
USPC ..... Plt./479

(58) Field of Classification Search
USPC ..... Plt./479
See application file for complete search history.

*Primary Examiner* — Susan McCormick Ewoldt
(74) *Attorney, Agent, or Firm* — Penny J. Aguirre

(57) ABSTRACT

A new cultivar of *Sedum* plant named 'Lime Zinger' characterized by its lime-green leaves with red picotee margins with the coloration retained for 7 months during the growing season, its production of 30 to 40 crowns the first year after vernalization, its heavy self-branching habit without being pinched, its numerous large (10 cm in diameter) inflorescences with flowers that are pink in color, and its disease free foliage.

2 Drawing Sheets

Botanical classification: *Sedum* hybrid.
Variety denomination: 'Lime Zinger'.

CROSS REFERENCE TO A RELATED APPLICATION

This application is co-pending with a U.S. Plant Patent Application filed for a plant derived from the same breeding program that is entitled *Sedum* Plant Named 'Cherry Tart' (U. S. Plant patent application Ser. No. 13/573,625).

BACKGROUND OF THE INVENTION

The present invention relates to a new and distinct cultivar of *Sedum* plant, botanically of hybrid origin and known as *Sedum* 'Lime Zinger' referred to hereinafter by its cultivar name, 'Lime Zinger'. The new cultivar of *Sedum* is a hardy herbaceous perennial grown for use as a landscape and container plant and is particularly suitable as a groundcover.

'Lime Zinger' arose from an ongoing breeding program by the Inventor in Hudsonville, Mich. The objective was to obtain a new cultivar of *Sedum* with lime green leaves with red picotee margins combined with a compact mounded habit without the tendency to flop open in the center of the plant.

The new cultivar arose from a controlled cross made in July of 2009 between unnamed plants from the Inventors breeding program as male and female parents. The Inventor selected 'Lime Zinger' as a single unique plant in September of 2010 from the resulting seedlings.

Asexual reproduction of the new cultivar was first accomplished by tip stem cuttings in July of 2010 in Hudsonville, Mich. Propagation by cuttings and crown division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Lime Zinger' as a unique cultivar of *Sedum*.

1. 'Lime Zinger' exhibits lime-green leaves with red picotee margins with the coloration retained for 7 months during the growing season.
2. 'Lime Zinger' exhibits 30 to 40 crowns the first year after vernalization (unique for a groundcover type *Sedum*).
3. 'Lime Zinger' exhibits a heavy self-branching habit without being pinched (unique for a groundcover type *Sedum*).
4. 'Lime Zinger' exhibits numerous large (10 cm in diameter) inflorescences with flowers that are pink in color.
5. 'Lime Zinger' exhibits disease free foliage; no leaf scorch or leaf blight has been observed in 3 years of trials.

The female parent differs from 'Lime Zinger' in being much shorter in height (70% shorter), and in having much smaller inflorescences, blue-gray foliage and much smaller leaves. The male parent differs from 'Lime Zinger' in being much taller in height and in having an upright plant habit, blue-gray foliage, and leaves that are larger in size. 'Lime Zinger' can be most closely compared to typical plants of *Sedum sieboldii*, *Sedum* 'John Creech' (not patented) and 'Cherry Tart'. *Sedum sieboldii* is similar to 'Lime Zinger' in having a groundcover plant habit and in having leaves with picotee red edges. *Sedum sieboldii* differs from 'Lime Zinger' in having blue-grey leaves, smaller flower heads, a much later blooming period (October) and in showing more variability as it is grown as a seed strain. 'John Creech' is similar to 'Lime Zinger' in having a groundcover plant habit and having green colored leaves. 'John Creech' differs from 'Lime Zinger' in having smaller leaves that lacking red picotee leaf margins, smaller less numerous flower heads that bloom 6 to 8 weeks earlier in early summer, and in being shorter in height with a less vigorous plant habit. 'Cherry Tart' differs from 'Lime Zinger' most significantly in having red leaves and in having less branched stems.

BRIEF DESCRIPTION OF THE DRAWINGS

The accompanying colored photographs illustrate the overall appearance and distinct characteristics of the new *Sedum*.

The photograph in FIG. 1 was taken of a plant about 15 months in age as grown in a trial garden in Hudsonville, Mich. and provides a view of 'Lime Zinger' in bloom.

Figure 1:
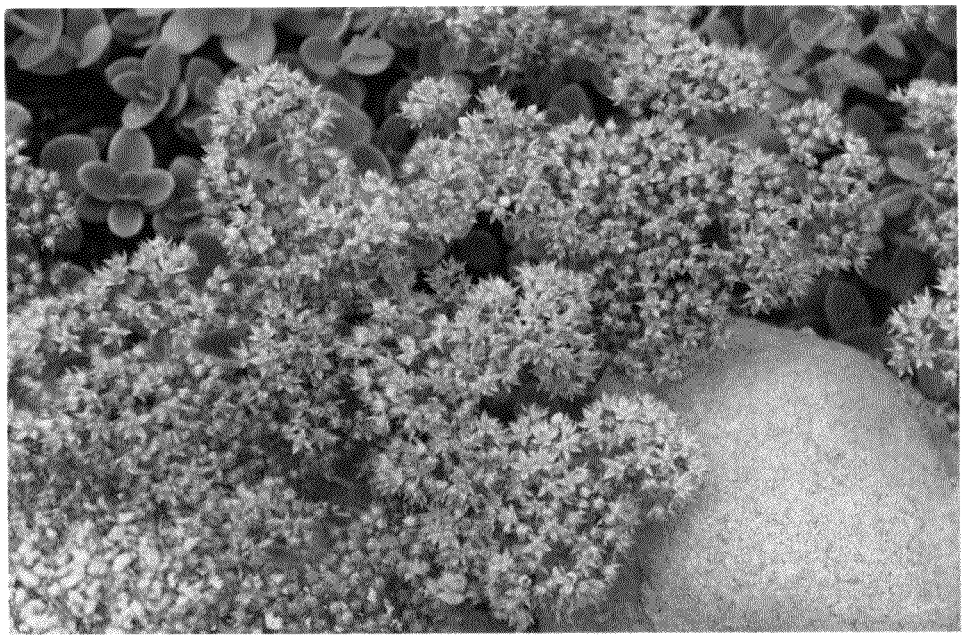
Figure 2:
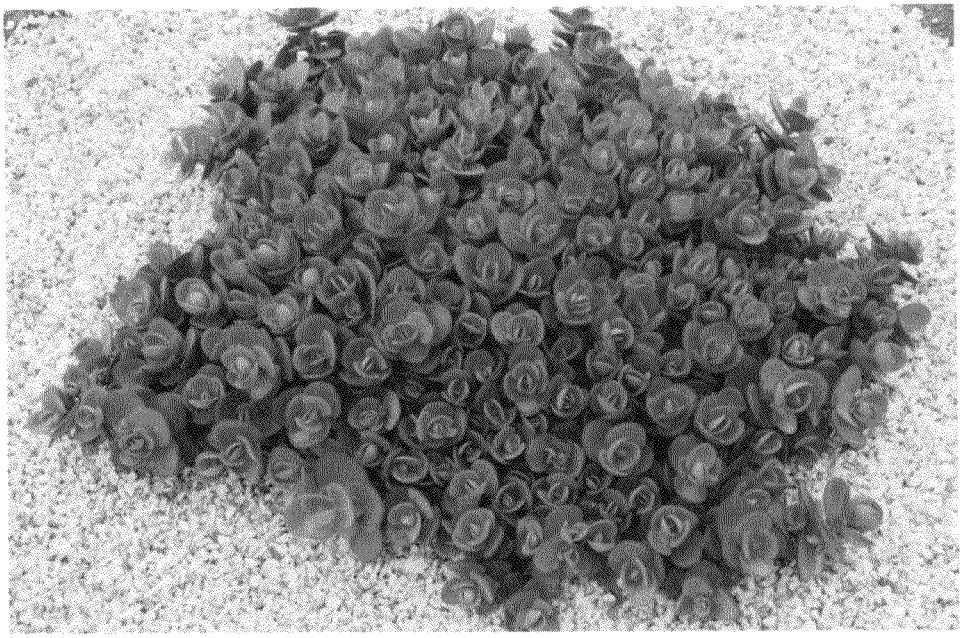
Figure 3:
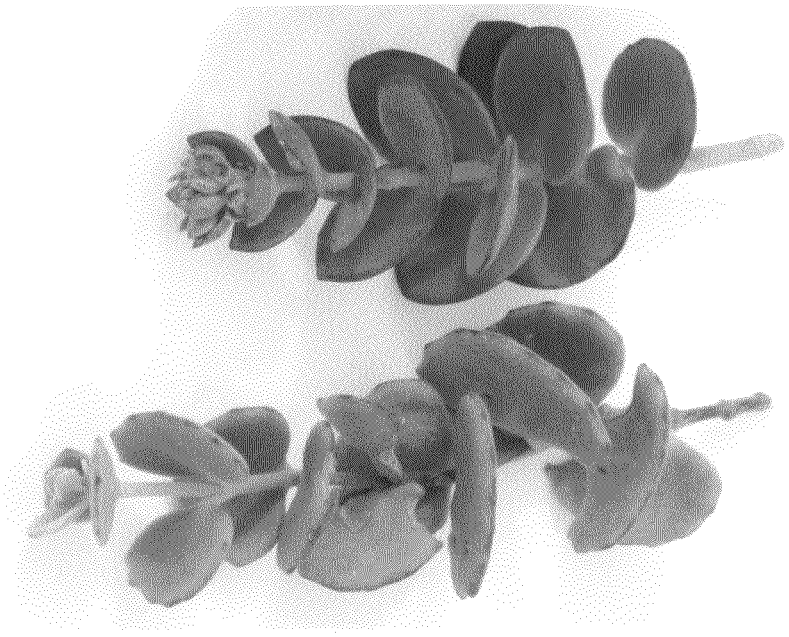

The photographs in FIG. 2 and FIG. 3 were taken of plants about 12 months in age. The photograph in FIG. 2 was taken in May and provides a view of the foliage of 'Lime Zinger'. The photograph in FIG. 3 was taken in July and provides a comparison between a stem of 'Lime Zinger' (top) and *Sedum sieboldii* (bottom) and illustrates the emergence of flower buds on 'Lime Zinger' and the lack of flower buds on *Sedum sieboldii*.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 15 month-old plants of 'Lime Zinger' as grown in the ground Hudsonville, Mich. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—5 weeks in mid to late summer.

*Plant type.*—Herbaceous perennial.

*Plant habit.*—Compact, mound, well-branched, groundcover of medium growing height for *Sedums*.

*Height and spread.*—Reaches about 15 cm in height and about 45 cm in spread.

*Hardiness.*—At least hardy in U.S.D.A. Zones 4 to 9.

*Diseases pest.*—Highly resistant to *sedum* foliage blight and leaf scorch, no occurrence of either has been observed in a 3 year period.

*Root description.*—Fibrous.

*Propagation.*—Tip stem cuttings.

*Growth rate.*—Vigorous.

Stem description:

*Stem shape.*—Slightly oval.

*Stem size.*—Averages 12 cm in length (including terminal peduncle) and about 2.5 mm in width with lateral branches an average of 8 cm in length and 2.5 mm in width.

*Internode length.*—Average of 1.3 cm.

*Stem color.*—Spring; 159A with a slight tint of 59B and becoming a blend of 145B 145C with a slight tint of 59B towards base, mid summer; a blend of 145B and 145C.

*Stem surface.*—Glabrous.

*Branching habit.*—Basal and lateral branching; about 5 to 8 branches per basal branch.

Foliage description:

*Leaf shape.*—Ovate-orbicular.

*Leaf division.*—Simple.

*Leaf arrangement.*—Whorled (sometime opposite).

*Leaf base.*—Cordate around stem.

*Leaf apex.*—Broadly acute-rounded.

*Leaf venation.*—Not conspicuous, color matched leaf color.

*Leaf margins.*—Entire.

*Leaf attachment.*—Sessile.

*Leaf orientation.*—Nearly horizontal to slightly upward, slightly cupped.

*Leaf texture.*—Thick, succulent.

*Leaf surface.*—Glandular and slightly glaucous.

*Leaf color.*—Spring upper and lower surface; 137B blending at very base with N144C, very thin picotee margins of 59C, mid summer and fall upper and lower surface, 137C with thin picotee margins of 59B.

*Leaf size.*—Average of 1.8 cm in length and 1.3 cm in width.

Flower description:

*Inflorescence type.*—Dense, slightly rounded cymes with an average of 5 terminal forked branches at terminus and upper lateral nodes.

*Inflorescence size.*—An average of 10 cm in diameter and 5 cm in depth (inclusive of all branches per stem).

*Lastingness of inflorescence.*—About one month.

*Flower type.*—Perfect, spreading, 5-starred.

*Flower number.*—An average of 30 flowers per branched cyme, about 150 flowers per stem.

*Flower fragrance.*—None.

*Flower buds.*—Oval in shape, about 4 mm length and 2 mm in diameter, ribbed surface, color; a blend of 155A and 63C with slight markings of N79B.

*Flower size.*—About 5 mm in depth and 7 mm in diameter.

*Peduncles.*—Slightly oval in shape, average of 4 cm in length, an average of 2 mm in width, secondary average 1.5 cm in length and 1.5 mm in width, 145B in color, glabrous surface, peduncle leaves; an average of 2 per individual cyme, elliptic in shape, an average of 1.6 cm in length and 6 mm in width, 137C in color with thin margin of 59B, glandular and slightly glaucous on both surfaces.

*Pedicels.*—Slightly oval in shape, an average of 2.5 cm in length and 1 mm in width, 145A in color, glabrous surface.

*Calyx.*—5-parted fused to tubular base, tips held nearly upright, about 2 cm in length and 2 cm in width.

*Sepals.*—5, tube; about 0.7 mm in length and 1.5 mm in width, 145A in color, tips about 2 mm in length and 1 cm in width, lanceolate in shape, 145A in color with very tips 178A on both surfaces, entire margin, narrowly acute apex, fused base, glaucous on both surfaces.

*Petals.*—5, spreading, 4 mm in length and 1.5 mm in width, lanceolate in shape, truncate base, acute apex, entire margin, color of inner and outer surfaces when opening; 155A and tingled with 63C, color when mature; 65C, becoming dry and upright and infused with 64C, translucent, glabrous on both surfaces.

Reproductive organs:

*Pistils.*—5, showy, held erect, about 4 mm in length, stigma; 0.5 mm in width and 63D in color, style; 3.5 mm in length, 1.5 mm in width, lanceolate in shape and 155A in color, ovary; small, single celled and translucent in color.

*Stamens.*—10, about 4 mm in length, filament; very fine and 155A in color and slightly suffused with 63C near tip, anther; acorn-shaped, about 0.5 mm in length and width and 59A in color, pollen is moderate in quantity and about 11D in color.

*Fruit*.—Fruit and seed production has not been observed.

It is claimed:

1. A new and distinct variety of *Sedum* plant named 'Lime Zinger' as described and illustrated herein.

* * * * *